United States Patent [19]
Salimbeni et al.

[11] Patent Number: 5,538,987
[45] Date of Patent: Jul. 23, 1996

[54] IMIDAZOLE ETHERS HAVING A II ANTAGONIST ACTIVITY

[75] Inventors: Aldo Salimbeni; Renato Canevotti; Jacques Mizrahi; Carlo Scolastico, all of Milan, Italy

[73] Assignee: Istituto Luso Farmaco D'Italia S.p.A., Milan, Italy

[21] Appl. No.: 374,696

[22] PCT Filed: Jul. 20, 1993

[86] PCT No.: PCT/EP93/01909

§ 371 Date: Jan. 25, 1995

§ 102(e) Date: Jan. 25, 1995

[87] PCT Pub. No.: WO94/02467

PCT Pub. Date: Feb. 3, 1994

[30] Foreign Application Priority Data

Jul. 28, 1992 [IT] Italy .................................. MI92A1832

[51] Int. Cl.$^6$ ..................... A61K 31/44; A61K 31/415; C07D 401/12; C07D 233/54
[52] U.S. Cl. ..................... 514/341; 514/381; 514/382; 514/397; 514/400; 546/275.1; 546/256; 546/269.7; 546/270.4; 548/252; 548/315.1; 548/315.4; 548/341.1; 548/342.1
[58] Field of Search ............................. 548/341.1, 342.1, 548/252, 315.1, 315.4; 546/278; 514/341, 381, 382, 397, 400

[56] References Cited

U.S. PATENT DOCUMENTS 5,187,271  2/1993  Bovy et al. ........................ 548/314.7

FOREIGN PATENT DOCUMENTS

| | | |
|---|---|---|
| 0253310 | 1/1988 | European Pat. Off. . |
| 0465368 | 1/1992 | European Pat. Off. . |
| 0540400 | 5/1993 | European Pat. Off. . |
| 9306828 | 4/1993 | WIPO . |

OTHER PUBLICATIONS

THE JOURNAL OF PHARMACOLOGY AND EXPERIMENTAL THERAPEUTICS, vol. 252, No. 2, Feb. 1990, pp. 711–718, A. T. Chie, et al, "Nonpeptide angiotensin II receptor antagonists. VII. Cellular and biochemical pharmacology of DuP 753, an orally antihypertensive agent"—See p. 711, Table 1 (Baltimore, MD, U.S.A.).

Primary Examiner—Robert W. Ramsuer
Assistant Examiner—Laura L. Stockton
Attorney, Agent, or Firm—Griffin, Butler Whisenhunt & Kurtossy

[57] ABSTRACT

Compounds of general formula (I)

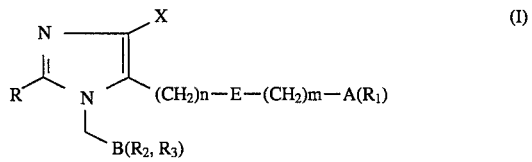

wherein E is O or S; R is $C_1$–$C_5$ straight, branched or cyclic alkyl or $C_2$–$C_5$ alkenyl; X can be H, F, Cl, Br, I, $CF_3$; n is an integer 1 to 4; m is an integer 0 to 4; A and B are 5- or 6- membered aromatic carbocyclic rings optionally containing one or more heteroatoms selected from N, O, S and carrying the substituents $R_1$, $R_2$ and $R_3$, respectively; $R_1$ can be hydrogen, halogen, $C_1$–$C_4$ alkoxycarbonyl, a sulfonic group or a tetrazole group of formula

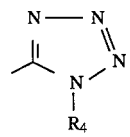

or

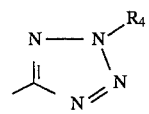

wherein $R_4$ can be hydrogen or $C_1$–$C_5$ alkyl; $R_2$ can be hydrogen or a $COOR_4$ group (wherein $R_4$ is hydrogen or $C_1$–$C_5$ alkyl), CN, $SO_3H$, $PO_3H$ or a tetrazole group $R_3$; can be a hydrogen or a moiety of formula (II)

$$B'(R'_2, R'_3) \qquad (II)$$

wherein: $B^1$, $R^1{}_2$ have the same meanings reported above for B and $R_2$, $R'_3$ is H; with the proviso that when A is phenyl, $R_1$ is different from H, and the pharmaceutically acceptable salts thereof.

6 Claims, No Drawings

IMIDAZOLE ETHERS HAVING A II ANTAGONIST ACTIVITY

This application is a 371 of PCT/EP93/01909 filed Jul. 20, 1993.

The present invention relates to imidazole ethers and thioethers having A II antagonist activity, the processes for the preparation thereof, pharmaceutical compositions containing them and the use thereof as therapeutical agents.

The renin-angiotensin system (RAS) is a proteolytic chain which plays a paramount role in the control of blood pressure and is apparently involved in the onset and the maintainement of some cardiovascular disorders, such as hypertension and cardiac decompensation.

The octapeptide hormon angiotensin II (A II), the final product from RAS, mainly forms in the blood following to the degradation of angiotensin I, carried out by the ACE enzyme, which is located in endothelium of blood vessels, lungs, kidney and many other organs. Such an hormon exerts a strong vasoconstricting action on arteries, due to its interaction with specific receptors located on the cell membranes.

One of the possible ways to control RAS is the A II antagonism at the receptor level. Some peptide analogues of A II (for example saralasin, sarmesin) are known to competitively block the interactions of said hormon, however the use thereof, both experimentally and clinically, is restricted by a partial agonist activity and by the lack of activity by the oral route.

Recently, a number of derivatives having a not-peptide structure were described to have II antagonist activity.

Examples of these compounds are reported in EP 253, 310, EP 324,377, EP 424,317, EP 419,048, EP 446,062, EP 403,159, EP 427,463, EP 434,249 and in papers by J. V. Duncia et al., J. Med. Chem. 33, 1312, (1990), 33, 1330 (1990), 34, 2525 (1991); J. Weinstock et al., J. Med. Chem. 34, 1514 (1991); A. P. Thomas et al., J. Med. Chem., 35, 877 (1992); D. Middlemiss et al., Bioorg. Med. Chem. Lett. 1, 711 (1991).

The present invention relates to novel imidazole derivatives having an aryl (heteroaryl)oxy (thio) alkyl or aryl (heteroaryl) alkoxy (alkylthio) alkyl moiety at the 5-position.

These novel compounds have A II antagonist properties and therefore they can be used in various cardiovascular disorders, such as hypertension, acute and chronic cardiac decompensations, intraocular hypertension, and in some renal diseases.

The compounds of the invention have general formula (I):

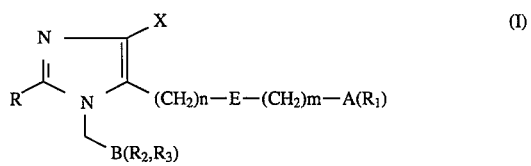

wherein:
E is O or S;
R is $C_1$–$C_5$ straight, branched or cyclic alkyl or $C_2$–$C_5$ alkenyl;
X can be H, F, Cl, Br, I, $CF_3$;
n is an integer 1 to 4;
m is an integer 0 to 4;
A and B are 5- or 6-membered aromatic carbocyclic rings optionally containing one or more heteroatoms selected from N, O, S and carrying the substituents $R_1$, $R_2$ and $R_3$, respectively;

$R_1$ can be hydrogen, halogen, $C_1$–$C_5$ alkyl, alkoxy, hydroxyl, carboxyl, $C_1$–$C_4$ alkoxycarbonyl, a sulfonic group or a tetrazole group of formula

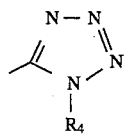

or

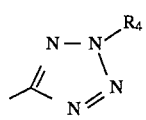

wherein $R_4$ can be hydrogen or $C_1$–$C_5$ alkyl; $R_2$ can be hydrogen or a $COOR_4$ group (wherein $R_4$ is hydrogen or $C_1$–$C_5$ alkyl), CN, $SO_3H$, $PO_3H$ or a tetrazole group;
$R_3$ can be hydrogen or a moiety of formula II $$B'(R'_2, R'_3) \tag{II}$$

wherein:
B',$R'_2$ have the same meanings reported above for B and $R_2$, $R'_3$ is H; with the proviso that when A is phenyl, $R_1$ is different from H.

This invention also relates to the salts of the compounds of formula I with organic and inorganic acids and bases. Said salts include ammonium salts, salts with alkali metals such as sodium and potassium, salts with alkaline earth metals such as calcium and magnesium, salts with organic bases such as dicyclohexylamine, N-methyl-D-glucamine, salts with amino acids such as arginine, lysine and the like. The salts with organic and inorganic acids comprise hydrochloric, hydrobromic, sulfuric, phosphoric, methanesulfonic, toluenesulfonic, maleic, fumaric, camphorsulfonic acids and the like.

Examples of $C_1$–$C_5$ alkyl groups are methyl, ethyl, propyl, isopropyl, butyl, isobutyl, tert-butyl, pentyl, isopentyl; preferably butyl.

Examples of $C_2$–$C_5$ alkenyl groups are vinyl, allyl, isoprenyl, 2-butenyl, 3-pentenyl.

Examples of $C_1$–$C_4$ alkoxycarbonyl groups are methoxycarbonyl, ethoxycarbonyl, propoxycarbonyl, butoxycarbonyl.

Examples of 5- or 6-membered or heterocyclic rings are phenyl, furan, oxazole, isoxazole, furazane, furodiazole, thiophene, thiazole, 1,3,4-thiadiazole, pyrrole, pyrazole, imidazole, triazoles and tetrazoles, pyridine, pyridazine, pyrimidine, pyrazine, triazine.

Preferred compounds of formula (I) are those in which $A(R_1)$ is an aryl or heteroaryl ring selected from phenyl, thiophene, furan and pyridine, optionally substituted with an halogen atom, a $C_1$–$C_4$ alkyl group, a $C_1$–$C_4$ alkoxy, hydroxyl, carboxyl, $C_1$–$C_4$ alkoxycarbonyl or tetrazole group.

Particularly preferred are the compounds of formula (I) in which $A(R_1)$ is an aryl or heteroaryl ring selected from phenyl, thiophene, furan and pyridine, optionally substituted with an halogen atom, a $C_1$–$C_4$ alkyl group, a $C_1$–$C_4$ alkoxy, hydroxyl, carboxyl, $C_1$–$C_4$ alkoxycarbonyl or tetrazole group and $R_2$ can be hydrogen or a $COOR_4$ group, wherein $R_4$ is as defined above; $R_3$ is hydrogen or an aryl or heteroaryl ring selected from phenyl, furan, thiophene, pyridine, thiazole optionally substituted with a carboxyl, $C_1$–$C_4$ alkoxycarbonyl, tetrazole group; n can be 1 or 2; m is an integer 0 to 2.

3

Most preferred compounds are the following ones:

2-butyl-1-[(2'-carboxy-1,1'-biphenyl-4-yl)methyl]-5-[(3-carboxythien-2-yl)methoxymethyl]-4-chloro-1H-imidazole 2-butyl-5-[(2-carboxyphenyl)methoxymethyl]-4-chloro-1-[[2'-(1H-tetrazol-5-yl)-1,1'-biphenyl-4-yl]methyl]-1H-imidazole 2-butyl-5-[(3-carboxythien-2-yl)methoxymethyl]-4-chloro-1-[[2'-(1H-tetrazol-5-yl)-1,1'-biphenyl-4-yl]methyl]-1H-imidazole 2-butyl-5-[(3-carboxyfuran-2-yl)methoxymethyl-4-chloro-1-[[2'-(1H-tetrazol-5-yl)-1,1'-biphenyl-4-yl]methyl]-1H-imidazole 2-butyl-4-chloro-5-[(pyridin-2-yl)methoxymethyl]-1-[[2'-(1H-tetrazol-5-yl)-1,1'-biphenyl-4-yl]methyl]-1H-imidazole 2-butyl-4-chloro-5-(2-pyridyloxymethyl)-1-[[2'-( 1H-tetrazol-5-yl)-1,1'-biphenyl-4-yl]methyl]-1H-imidazole 2-butyl-1-[(2'-carboxy-1,1'-biphenyl-4-yl)methyl]-5-[(3-carboxyfuran-2-yl)methoxymethyl]-4-chloro-1H-imidazole 2-butyl-1-[(2'-carboxy-1,1'-biphenyl-4-yl)methyl]-5-[(2-carboxyphenyl)methoxymethyl]-4-chloro-1H-imidazole 2-butyl-1-[(2'-carboxy-1,1'-biphenyl-4-yl)methyl]-5-[(4-carboxyphenyl)methoxymethyl]-4-chloro-1H-imidazole 2-butyl-1-[(2'-carboxy-1,1'-biphenyl-4-yl)methyl]-5-[(2-carboxyphenoxy)methyl]-4-chloro-1H-imidazole 2-butyl-5-[(2-carboxyphenyl)methoxymethyl]-1-[[2-(2-carboxyphenyl)thien-5-yl]methyl]-4-chloro-1H-imidazole 2-butyl-5-[(2-carboxyphenyl)methoxymethyl]-1-[[4-(2-carboxyfuran-3-yl)phenyl]methyl]-4-chloro-1H-imidazole 2-butyl-1-[(4-carboxyphenyl)methyl]-1-[( 2-carboxyphenyl)methoxymethyl]-4-chloro-1H-imidazole 2-butyl-4-chloro-5-[(2-methoxycarbonylphenyl) methoxymethyl] -1-[[2'-(1H-tetrazol-5-yl)-1,1'-biphenyl-4yl]methyl]-1H-imidazole 2-butyl-4-chloro-5-[(3-methoxycarbonylfuran-2-yl)methoxymethyl]-1-[[2'-(1H-tetrazol-5-yl)-1,1'-biphenyl-4-yl]methyl]-1H-imidazole 2-butyl-4-chloro-5-[(3-methoxycarbonylthien-2-yl)methoxymethyl]-1-[[2'-(1H-tetrazol-5-yl)-1,1'-biphenyl-4-yl]methyl]-1H-imidazole.

Moreover, the invention relates to the processes for the preparation of the compounds of general formula (I). According to the invention, the compounds of general formula (I) can be prepared as described in Scheme I, in which three possible processes (A, B and C) are described.

SCHEME I

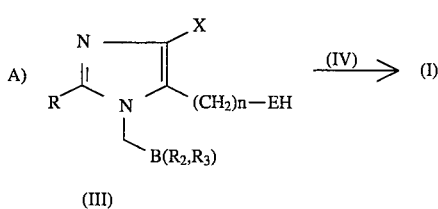

(III)

4
-continued
SCHEME I

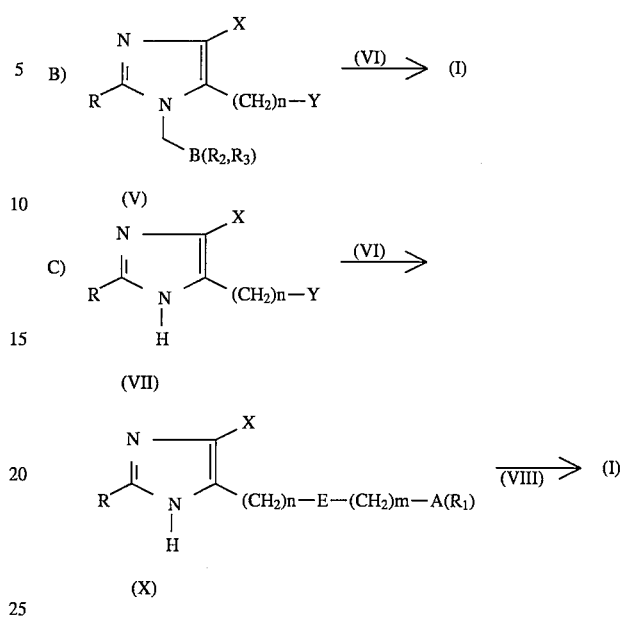

(X)

According to process A, 5-hydroxyalkyl- or 5-mercaptoalkyl- imidazoles of general formula (III), in which B, E, R, $R_3$, X, n have the meanings reported above, whereas $R_2$ can be CN, $COOR_4$ (with $R_4$ the same as $C_1$-$C_5$ alkyl), or a suitably protected tetrazole, sulfonic or phosphoric group, are reacted with the compounds of general formula (IV)

$$Y\text{-}(CH_2)_m\text{-}A(R_1) \hspace{2cm} (IV)$$

wherein Y can be halogen, tosyl, mesyl and m, A, $R_1$ have the meanings reported above. The reaction is suitably carried out in the presence of alkali or alkaline-earth hydroxides or hydrides, using suitable solvents such as THF, DMF etc. or mixtures of aprotic solvents and water, if operating in phase transfer.

In process B, compounds (I) can also be prepared from the suitable imidazoles of general formula (V) by reaction with compounds of general formula (VI)

$$A(R_1)\text{-}(CH_2)_m\text{-}EH \hspace{2cm} (VI)$$

wherein A, $R_1$, m, E have the meanings reported above, in the presence of alkali or alkaline-earth metal hydroxides or hydrides, using suitable solvents.

Alternatively, according to process C, compounds of general formula (I) can be prepared by reacting imidazole derivatives of general formula (VII) with compounds of general formula (VI) in suitable solvents, under the already described conditions, to give the compounds of general formula (X), in which R, X, n, E, m, A, $R_1$ have the meanings reported above.

The subsequent reaction with compounds of general formula (VIII)

$$Y\text{-}CH_2\text{-}B(R_2,R_3) \hspace{2cm} (VIII)$$

wherein B, $R_2$, $R_3$, Y, have the meanings reported above, Gives the compounds of formula (I), in a mixture with the corresponding regioisomers, which can easily be recovered by chromatographic techniques or crystallization.

The preparation of compounds in which $R_1$ or $R_2$ are independently carboxyl or tetrazole groups can be effected in various ways. When $R_1$ or $R_2$ are an alkoxycarbonyl group, compound (I) can be subjected to either acidic (by hydrochloric, trifluoroacetic, formic, acetic acids in protic solvents, such as water-lower alcohols mixtures, or in aprotic solvents such as $CH_2Cl_2$, dioxane) or alkaline hydrolysis (with alkali hydroxides in water-lower alcohols mixtures at a temperature ranging from 20° to 80° C.).

When $R_1$ or $R_2$ is a CN group, this can be subjected to hydrolysis by treatment with strong acids or bases, preferably with 1:1 mixtures of aqueous hydrochloric acid and glacial acetic acid under reflux or with NaOH in ethyl alcohol or ethylene glycol at a temperature ranging from 20° C. to the reflux one.

The CN group can be converted into the corresponding tetrazole derivative by treatment with $NaN_3$ and $NH_4Cl$ in DMF at temperatures ranging from 30° to 120° C., or better still by 1,3-dipolar cycloaddition of trialkyl or triaryl tin azides in solvents such as toluene or xylene at temperatures ranging between 110° and 130° C.

When $R_2$ is a tetrazole group protected with a triphenylmethyl group, the latter can be removed by treatment with acetic, trifluoroacetic or hydrochloric acid or by hydrogenolysis.

The intermediates of general formula (IV) and (VI), used in the etherification reactions, were prepared by methods known in literature. For example, the derivatives (IV) in which A is a furan or thiophene ring, $R_1$ is $COOCH_3$, y is bromine and m=1, were prepared by esterification of the corresponding 3-carboxy-2-methylfurans prepared according to the method described by D. W. Knight et al. J. Chem. Soc. (1983) 791–794, and subsequent halogenation with bromosuccinimide.

The substituted imidazole derivatives of general formula (III) and (V)

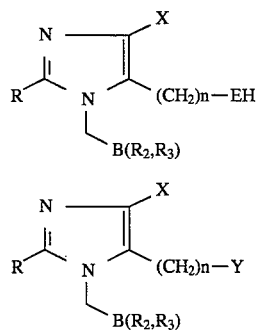

can be obtained by alkylation of the imidazoles of formula (IX)

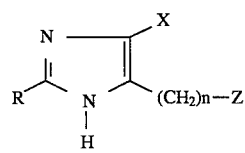

wherein Z is a EH group or a CHO group, with a compound of formula (VIII) and possible subsequent transformation of the group Z into the group Y. The reaction can be carried out on the imidazole derivatives in form of sodium or potassium salts, in an aprotic solvent such as DMF or DMSO. The imidazole salt can be prepared either by reaction with a sodium or potassium alkoxide in an alcoholic or aprotic solvent such as DMF or in situ in the presence of a base such as $Na_2CO_3$ in DMF. These alkylation techniques give mixtures of the 2 regioisomers, since the alkylation can take place at both the imidazole nitrogen atoms. The regioisomers are easily separated by chromatographic techniques or by crystallization. If the alkylation is carried out on the corresponding 4-chloro-5-formyl imidazoles, the regioisomer alkylated at the nitrogen atom adjacent to the aldehyde group is mainly obtained. The reduction of the latter with $NaBH_4$ or analogues reagents and the possible transformation into halides, tosyl derivatives or thiols, gives compounds of formula (III) and (V).

The imidazole compounds of formula (IX) are obtained using methods known in literature, for example by reacting the suitable imidates with dihydroxy ketones in liquid ammonia, as described by P. Dziurion et al. in Archiv. Pharmaz. 307 470–473 (1974). The halogenation of the imidazole ring is obtained using N-halosuccinimide in solvents such as dioxane, THF or 2-methoxyethanol.

The biphenyl or heteroarylphenyl derivatives of general formula (VIII) can be prepared either by biaryl coupling in the presence of copper according to one of the methods described in literature (see for example P.Fanta/Synthesis (1974) 9–21) or by the action of aryl Grignard compounds on 2-methoxyphenyloxazolines according to the method described by A. Meyers et al. in J.Org.Chem. 43, 1372–1379. Alternatively, the derivatives of general formula (VIII) can be prepared by biaryl coupling catalyzed by Ni or Pd complexes, as described by E. Negishi et al in Org. Synt. (1987) 67–74, by coupling of arylboronic acids with aryl triflates catalyzed by Pd complexes, as described by V. Snieckus et al. in Tetr.Lett. 31 1665–1668 (1990) or by condensation of aryl or heteroaryl cuprates with haloaryls as described by H. Nilsson et Al. in Acta Chem. Scand. 24, 2379 (1970). In the preparation of furan and pyrrole rings, methods for the cyclization of γ-diketones or protected β-epoxyaldehydes can be used (for example according to D. M. Burness J.O.C. 21, (1956), 102), whereas the usual cyclizations of α-halogen-β-ketoesters with thioamido derivatives have been used for the synthesis of thiazole derivatives.

The compounds described in the present invention act as antagonists at the A II receptor level.

For the characterization and the evaluation of the effectiveness of the compounds of the invention, in vitro tests (such as the inhibition of the A II-induced contraction in the rabbit aorta and the displacement of $^{125}I$-Sar$^1$-Ile$^8$-AT II or [$^3$H] AT II in the rat adrenal cortex) and an in vivo test (the inhibition of the A II-induced pressory response in the ganglio-blocked normotensive rat) were selected. The compounds of invention have shown a remarkable activity in the above tests; for example, in the in vitro tests, a number of compounds turned out to have $pA_2$ values higher than 6.5, whereas they showed to have a Ki<1 μM in the receptor binding test.

For example the compound 2-butyl-5-[( 2-carboxyphenyl)methoxymethyl]-4-chloro-1-[[2'- (1H-tetrazol-5-yl)-1, 1'-biphenyl-4-yl]methyl]-1H-imidazole (ex. 18) have shown Ki=4.4 nM and $pA_2$=9.7, while 2-butyl-5-[(3-carboxyfuran-2-yl)methoxymethyl]-4-chloro-1-[[2'-(1H-tetrazol-5-yl)-1, 1'-biphenyl-4-yl]methyl]-1H-imidazole (ex. 18) have shown Ki=3.2 nM and $pA_2$=8.9.

The compounds (I) or the pharmaceutically acceptable salts thereof can be used in pharmaceutical preparations, alone or in a mixture with pharmaceutically acceptable excipients, for the oral or parenteral administrations. Suitable excipients are for example starch, lactose, glucose, arabic gum, stearic acid and the like. The pharmaceutical preparations can be in solid form such as tablets, capsules or suppositories or in liquid form, such as solutions, suspensions or emulsions.

Moreover, if administered parenterally, the pharmaceutical preparations can be in form of sterile solutions.

The compounds (I) can be administered in unit doses ranging from 1 to 100 mg to patients suffering from cardiac and vascular disorders, such as hypertension, acute and chronic cardiac decompensation, intraocular hypertension. However, a use can be envisaged also for other disorders, such as secondary hyperaldosteronism, pulmonary hypertension, renal diseases (glomerulonephritis, diabetic nephropathy) or vascular disorders (hemicrania, Raynaud's disease).

The following examples further illustrate the invention. M.p. are not corrected; the identity of the substances was established by means of elementary analysis (C, H, N) and IR, UV, NMR (200 MHz) and mass spectroscopies. Flash chromatographies (FC) were carried out on silica gel according to the procedures by W. C. Still, J.Org.Chem. 43, 2923 (1978).

EXAMPLE 1

Methyl 2-(5-methylthien-2-yl)benzoate

A solution of 9.8 g of 2-methylthiophene in 100 ml of anhydrous ether is added with 62 ml of 1.6 M BuLi in hexane. The mixture is left under stirring for 1 h and the resulting solution is added to a solution of 14.6 g of anhydrous $ZnCl_2$ in 240 ml of 2:1 THF/$Et_2O$.

After 2h stirring, the resulting solution is slowly dropped into a solution of 1.26 g of $Ni(Ph_3P)_2Cl_2$ and 15 g of methyl 2-bromobenzoate in 150 ml of anhydrous THF and left under stirring for 12 h. The resulting mixture is poured into in 0.5 N HCl cooled at 5° C. The phases are separated and the aqueous one is extracted with ether. The combined organic phases are washed with a NaCl saturated solution, dried and evaporated to dryness. The obtained crude compound is purified by F.C. (eluent: isopropyl ether:hexane 15:85) to obtain 14 g of a light yellow oil (85% yield). $^1$H NMR (CDCl$_3$), δ: 2.51 (d, 3 H), 3.77 (s, 3 H), 6.72 (m, 1 H), 6.83 (d, 1 H), 7.25–7.48 (m, 3 H), 7.68 (dd, 1 H).

The following compounds are prepared according to the same procedure:

2-(5-methylthien-2-yl)benzonitrile $^1$H NMR (CDCl$_3$), δ: 2.54 (d, 3 H); 6.81 (dd, 1 H); 7.277.72 (m, 5 H)

methyl 3- (4-methylphenyl) -2-thiophenecarboxylate $^1$H NMR (CDCl$_3$), δ: 2.39 (s, 3 H); 3.78 (s, 3 H); 7.08 (d, 1 H); 7.22 (d, 2 H); 7.35 (d, 2 H); 7.49 (d, 1 H)

methyl 4'-methyl-1,1'-biphenyl-2-carboxylate $^1$H NMR (CDCl$_3$), δ: 2.40 (s, 3 H); 3.67 (s, 3 H)-2-cyano-4'-methyl-1,1'-biphenyl $^1$H NMR (CDCl$_3$), δ: 2.42 (s, 3 H); 7.21–7.85 (m, 8 H); 7.22–7.83 (m, 8 H).

EXAMPLE 2

2-Bromomethyl-5-(2-methoxycarbonylphenyl)thiophene

A mixture of 10 g of methyl 2-(5-methylthien-2-yl) benzoate, 7.6 g of N-bromosuccinimide and a catalytic amount of benzoyl peroxide in 600 ml of $CCl_4$ is heated to 80° C. for 3 hours under stirring.

Succinimide is filtered off and the resulting solution is washed 3 times with $H_2O$, dried over $Na_2SO_4$ and evaporated to dryness under reduced pressure. 13 g of a brown oil are obtained (95% yield). $^1$H NMR (CDCl$_3$), δ: 3.76 (s, 3 H), 4.76 (s, 2 H), 6.85 (d, 1 H), 7.06 (d, 1 H), 7.35–7.52 (m, 3 H), 7.74 (dd, 1 H).

The following compounds are prepared according to the same procedure:

2-bromomethyl-5-[2-(1-triphenylmethyltetrazol-5-yl) phenyl]thiophene $^1$H NMR (CDCl$_3$), δ: 4.56 (s, 2 H); 6.55–7.89 (m, 21 H)

3-(4-bromomethylphenyl)-2-methoxycarbonylthiophene $^1$H NMR (CDCl$_3$), δ: 3.78 (s, 3 H); 4.54 (s, 2 H); 7.10–7.70 (m, 6 H)

2-bromomethyl-5-(2-methoxycarbonylphenyl)furan $^1$H NMR (CDCl$_3$), δ: 3.87 (s, 3 H); 4.53 (s, 2 H); 6.47 (d, 1 H); 6.53 (d, 1 H); 7.30–7.72 (m, 4 H)

3-(4-bromomethylphenyl)-2-methoxycarbonylfuran $^1$H NMR (CDCl$_3$), δ: 3.85 (s, 3 H); 4.52 (s, 2 H); 6.62 (m, 1 H); 7.3–7.7 (m, 5 H)

4-(4-bromomethylphenyl)-5-methoxycarbonyl-2-methylthiazole 2-bromomethyl-5-(2-methoxycarbonylphenyl)pyrrole 2-bromomethyl-5-[2-(1-triphenylmethyltetrazol-5-yl)phenyl]furan $^1$H NMR (CDCl$_3$), α: 4.21 (s, 2 H); 6.11 (d, 1 H); 6.27 (d, 1 H); 7.02–8.12 (m, 21 H)

3-(4-bromomethylphenyl)-2-( 1-triphenylmethyltetrazol-5-yl) thiophene 3-(4-bromomethylphenyl)-2-(1-triphenylmethyltetrazol-5-yl)furan methyl 4'-bromomethyl-1,1'-biphenyl-2-carboxylate methyl 4-bromomethylphenylcarboxylate 2-bromomethyl-3-methoxycarbonylthiophene $^1$H NMR (CDCl$_3$), δ: 3.88 (s, 3 H); 5.09 (s, 2 H); 7.21 (d, 1 H); 7.21 (d, 1 H); 7.41 (d, 1 H)

2-bromomethyl-3-methoxycarbonylfuran $^1$H NMR (CDCl$_3$), δ: 3.87 (s, 3 H); 4.81 (s, 2 H); 6.70 (d, 1 H); 7.39 (d (1 H)

2-bromomethylpyridine 5-(4'-bromomethyl-1,1'-biphenyl-2-yl)-1-triphenylmethyltetrazole $^1$H NMR (CDCl$_3$), δ: 4.39 (s, 2 H); 6.82–8.15 (m, 23 H).

EXAMPLE 3

5-[2-(5-methylthien-2-yl)phenyl]-1-triphenylmethyltetrazole

A mixture of 5 g of 2-(2-methylthien-5-yl)benzonitrile, 1.6 g of $NAN_3$, 8.1 g of tributyl tin chloride and 40 ml of toluene is heated under reflux for 80 hours. The resulting mixture is cooled, diluted with 20 ml of toluene and treated with 3 ml of 10 N NaOH and with 8.4 g of triphenylmethyl chloride. The obtained solution is stirred for 4 hours at room temperature, then 40 ml of hexane and 20 ml of $H_2O$ are added, the mixture is cooled to 0° C. and stirred for 2 h. The resulting solid is filtered, washed 2 times with $H_2O$, once with a toluene:hexane 60:40 mixture and vacuum dried. 6 g (50% yield) of an ivory solid are obtained. M.P. 182–184 (dec).

The following compounds are prepared according to the same procedure:

5-[2-(2-methylfuran-2-yl)phenyl]-1-triphenylmethyltetrazole $^1$H NMR (CDCl$_3$), δ: 2.05 (s, 3 H); 6.03–7.72 (m, 21 H)

5-[3-(4-methylphenyl)thien-2-yl]-1-triphenylmethyltetrazole

5-[3-(4-methylphenyl)furan-2-yl]-1-triphenylmethyltetrazole 5-(4'-methyl-1,1'-biphenyl-2-yl) -1-triphenylmethyltetrazole (m.p. 168°–170° C.) $^1$H NMR (CDCl$_3$), δ: 2.27 (s, 3 H); 6.35–7.92 (m, 23 H).

EXAMPLE 4

1-(2-Bromophenyl)-1,4-pentanedione

A mixture of 90 g of bromobenzaldehyde, 41 g of methyl vinyl ketone, 24.2 g of 3-benzyl-4-methyl-5-hydroxyethylthiazolium chloride is added with 45 ml of triethylamine. A marked exothermicity is observed, at the end of which the reaction mixture is heated to 70° C. under stirring for 4 h. The resulting mixture is cooled and partitioned between 800 ml of ether and 400 ml of $H_2O$. The aqueous phase is reextracted and the combined organic phases are washed with 10% HCl and with brine, then dried over $Na_2SO_4$ and the solvent is evaporated off. 110 g of an orange oil are obtained (93% yield). $^1H$ NMR ($CDCl_3$), δ: 2.22 (s, 3 H), 2.89 (t, 2 H), 3.15 (t, 2 H), 7.18–7.65 (m, 4 H).

EXAMPLE 5

2-Methyl-5-(2-bromophenyl)furan

A solution of 18 g of 1-(2-bromophenyl)-1,4-pentanedione and 1 g of p-toluenesulfonic acid in 200 ml of anhydrous benzene is heated under reflux over molecular sieves for 12 h. The resulting solution is washed 3 times with brine, dried over $Na_2SO_4$ and evaporated to dryness under reduced pressure. The residue is purified by FC (eluent hexane:acetate 95:5) and 12.2 of a light yellow oil are obtained g (70% yield). $^1H$ NMR ($CDCl_3$), δ: 2.38 (d, 3 H), 6.12 (m, 1 H), 7.1–7.4 (m, 3 H), 7.63 (dd, 1 H), 7.79 (dd, 1 H).

EXAMPLE 6

2-(5-Methylfuran-2-yl)benzoic acid

A solution of 10 g of 2-methyl-5-(2bromophenyl)furan dissolved in 120 ml of anhydrous THF and cooled at –70° C. is added with 28.4 ml of a 1,6 M solution of butyl lithium in hexane. The resulting red solution is stirred for 30 minutes at –70° C., then $CO_2$ is bubbled therein for 10 minutes. The mixture is warmed to room temperature and left to stand for 3 h. The solvent is evaporated and the obtained solid is triturated for 30 minutes with an hexane:ether 7:1 mixture. The resulting solid is dissolved in $H_2O$, acidified with HCl and extracted with ether. The organic phase is washed with brine, dried and evaporated to dryness. 8 g of a dark oil are obtained (95% yield). $^1H$ NMR ($CDCl_3$), δ: 2.33 (d, 3 H), 6.06 (dd, 1 H), 6.55 (d, 1 H), 7.29–7.90 (m, 4 H).

EXAMPLE 7

Methyl 2-(5-methylfuran-2-yl)benzoate

A solution of 4 g of 2-(5-methylfuran-2-yl)benzoic acid in 10 ml of $CH_3OH$ and 10 ml of $H_2O$ is added with a solution of 6.4 g of $Cs_2CO_3$ in 30 ml of $H_2O$ to pH 8. The solvent is evaporated and the residue is stripped more times with benzene.

The resulting solid is dissolved in 100 ml of 1:1 acetone:DMF, 6 g of methyl iodide are added thereto, stirring at 35° C. for 2 h. The solvents are evaporated and the residue is treated with $H_2O$ and extracted with ether. The organic phase is washed with brine, dried and evaporated to dryness under reduced pressure. The obtained residue is bulb distilled to obtain 3.3 of a colourless oil (79% yield). $^1H$ NMR ($CDCl_3$), δ: 2.33 (d, 3 H), 3.84 (s, 3 H), 6.06 (dd, 1 H), 6.47 (d, 1 H), 7.28–7.70 (m, 4 H).

EXAMPLE 8

Ethyl methyl 2-bromo-3-(4-methylphenyl)-3-oxopropanoate

A solution of 3.4 g of ethyl 3-(4-methylphenyl)-3-oxopropanoate (prepared according to the method described by V. H. Wallingford et al. in J.A.C.S. Vol. 69 2252–2254) in 30 ml of $CCl_4$ heated to 70° C. is slowly added with 2.6 g of $Br_2$ dissolved in 8 ml of $CCl_4$. After 30 minutes the solvent is evaporated off under reduced pressure to obtain 4.5 g of a dark fluid oil (96% yield). $^1H$ NMR ($CDCl_3$), δ: 1.23 (t, 3 H), 2.41 (s, 3 H), 4.26 (q, 2 H), 5.64 (s, 1 H), 7.28 (dd, 2 H), 7.88 (d, 2 H).

EXAMPLE 9

2-Methyl-4-(4-methylphenyl)-5-ethoxycarbonylthiazole

A solution of 4.4 g of ethyl 2-bromo-3-(4-methylphenyl)-3-oxopropanoate in 30 ml of anhydrous ethanol is added with 1.4 g of thioacetamide and the mixture is refluxed for 4 hours. The solvent is evaporated and the residue is dissolved in $H_2O$ and alkalinized to pH 10 with 10% NaOH, extracted 2 times with ether and the organic phase is washed with brine, dried and evaporated to dryness under reduced pressure. The residue is purified by F.C. (eluent 90:10 hexane:ethyl acetate) and 1.65 g of a light yellow solid are obtained (41% yield). $^1H$ NMR ($CDCl_3$), δ: 1.28 (t, 3 H), 2.39 (s, 3 H), 2.73 (s, 3 H), 4.26 (q, 2 H), 7.23 (d, 2 H), 7.62 (d, 2 H).

EXAMPLE 10

Methyl 2,3-epoxy-3-(4-methylphenyl)-5,5-dimethoxypentanoate

A solution of 7.9 g of 3,3-dimethoxy-1-(4-methylphenyl))-1-propanone (prepared according to the procedures described by E. Earl Royals in J.A.C.S. Vol.75 2050–2053) in 100 ml of anhydrous ether is added with 5.35 g of methyl chloroacetate. The reaction mixture is cooled to –10° C., 4.1 g of sodium methoxide are added in portions and the mixture is stirred at a temperature of 0° C. for 2 h and at room temperature for 3 h. The resulting mixture is cooled to 0° C. and 10% acetic acid is added until pH 5. The aqueous phase is extracted 3 times with ether, the organic phase is washed with brine, dried over $Na_2SO_4$ and evaporated to dryness under reduced pressure. 10.2 of a brown oil are obtained g (98% yield) which is used without further purification as diastereomeric mixture. $^1H$ NMR ($CDCl_3$) δ: 2.31–2.39 (2s, 3 H) 2.2–2.5 (m, 2 H), 3.23 (dq, 6 H), 3.47 (s, 1 H), 3.81 (d, 3 H), 4.35 (dt, 1 H), 7.1–7.32 (dd, 4 H).

EXAMPLE 11

Methyl 3-(4-methylphenyl)furan-2-carboxylate

A solution of 10.8 g of methyl 2,3-epoxy-3-(4-methylphenyl)-5,5-dimethoxypentanoate and 1.1 g of p-toluenesulfonic acid in 60 ml of anhydrous benzene is refluxed over molecular sieves for 3 h. 60 ml of ethyl acetate are added, the mixture is washed 2 times with 50 ml of a $NaHCO_3$ saturated aqueous solution, dried over $Na_2SO_4$ and the solvent is evaporated under reduced pressure. The residue is purified by F.C. to obtain 4.2 g of a yellow oil (50% yield). $^1H$ NMR ($CDCl_3$), δ: 2.39 (s, 3 H), 3.85 (s, 3 H), 6.62 (d, 1 H), 7.24 (d, 2 H), 7.48 (d, 2 H), 7.56 (d, 1 H).

EXAMPLE 12

2-Butyl-4-chloro-5-formyl-1-[(2-methoxycarbonyl-1,1'-biphenyl-4-yl)methyl]-1H-imidazole A mixture of 4.5 g of 2-butyl-4-chloro-5-formylimidazole and 6.75 g of $K_2CO_3$ in 200 ml of anhydrous DMF under nitrogen atmosphere is added under stirring with a solution of 8.1 g of methyl 4'-bromomethyl-1,1'-biphenyl-2-carboxylate in 10 ml of anhydrous DMF. The mixture is stirred at room temperature for 2 hours then concentrated under reduced pressure to 50 ml, poured into 500 ml of H$_2$O and extracted with CH$_2$Cl$_2$. The organic phase is washed with H$_2$O, dried over Na$_2$SO$_4$ and evaporated to dryness under reduced pressure. 9 of an orange oil are obtained which is used without further purification. $^1$H NMR (CDCl$_3$), δ: 0.89 (t, 3 H); 1.45 (m, 2 H); 1.72 (m, 2 H); 2.66 (m, 2 H); 3.62 (s, 3 H); 5.59 (s, 2 H); 7.02–7.88 (m, 8 H); 9.76 (s, 1 H).

The following compounds are prepared according to the same procedure:

2-butyl-4-chloro-5-formyl-1-[( 4-methoxycarbonylphenyl)methyl]-1H-imidazole $^1$H NMR (CDCl$_3$), δ: 0.86 (t, 3 H); 1.32 (m, 2 H); 1.63 (m, 2 H); 2.59 (t, 2 H); 3.90 (s, 3 H); 5.59 (s, 2 H); 7.08 (dd, 2 H); 7.99 (dd, 2 H); 9.74 (s, 1 H)

2-butyl-4-chloro-5-formyl-1-[[5-( 2-methoxycarbonylphenyl)thien-2-yl]methyl]-1H-imidazole $^1$H NMR (CDCl$_3$), δ: 0.94 (t, 3 H); 1.41 (m, 2 H); 1.78 (m, 2 H); 2.78 (t, 2 H); 3.72 (s, 3 H); 5.67 (d, 2 H); 6.85–8.05 (m, 6 H); 9.77 (s, 1 H)

2-butyl-4-chloro-5-formyl-1-[[5-( 2-methoxycarbonylphenyl)furan-2-yl]methyl]-1H-imidazole 2-butyl-4-chloro-5-formyl-1-[[2'-(1-triphenylmethyltetrazol-5-yl)-1,1'-biphenyl-4-yl]methyl]-1H-imidazole $^1$H NMR (CDCl$_3$), δ: 0.86 (t, 3 H); 1.32 (m, 2 H); 1.65 (m, 2 H); 2.52 (t, 2 H); 5.44 (s, 2 H); 6.82–8.01 (m, 23 H); 9.73 (s, 1 H).

EXAMPLE 13

2-butyl-4-chloro-5-hydroxymethyl-1-[( 2'-methoxycarbonyl-1,1'-biphenyl-4-yl)methyl]-1H-imidazole A solution of 4.8 g of 2-butyl-4-chloro-5-formyl-1-[(2'-methoxycarbonyl-1,1'-biphenyl-4-yl)methyl]-1H-imidazole in 100 ml of absolute ethanol is added with a solution of 0.44 g of NaBH$_4$ in 10 ml of ethanol. The mixture is stirred at room temperature for 1 hour then is acidified with glacial CH$_3$COOH to pH 4. The resulting solution is evaporated to dryness under reduced pressure and the residue is taken up into ether. The in soluble part is filtered, the ether solution is evaporated to dryness and the residue is stripped more times with toluene.

The crude obtained is separated by F.C. (eluent ethyl acetate/hexane 6:4). 4.6 of a colourless oil are obtained (96% yield). $^1$H NMR (CDCl$_3$), δ: 0.87 (t, 3 H); 1.35 (m, 2 H); 1.66 (m, 2 H); 2.59 (t, 2 H); 3.63 (s, 3 H); 4.50 (s, 2 H); 5.26 (s, 2 H); 7.05–7.9 (m, 8 H).

The following compounds are prepared according to the same procedure:

2-butyl-4-chloro-5-hydroxymethyl-1-[[2-( 2-methoxycarbonylphenyl)thien-5-yl]methyl]-1H-imidazole $^1$H NMR (CDCl$_3$), δ: 0.92 (t, 3 H); 1.41 (m, 2 H); 3.73 (s, 3 H); 4.62 (s, 2 H); 5.35 (s, 2 H); 6.81–7.78 (m, 6 H)

2-butyl-4-chloro-5-hydroxymethyl-1-[[4-( 2-methoxycarbonylfuran-3-yl)phenyl]methyl]-1H-imidazole 2-butyl-4-chloro-5-hydroxymethyl-1-[[2'- ( 1-triphenylmethyltetrazol-5-yl)-1,1'-biphenyl-4-yl]methyl]-1 H-imidazole $^1$H NMR (CDCl$_3$), δ: 0.85 (t, 3 H); 1.27 (m, 2 H); 1.64 (m, 2 H); 2.49 (t, 2 H); 4.29 (s, 2 H); 5.09 (s, 2 H); 6.70–7.98 (m, 23 H)

2-butyl-4-chloro-5-hydroxymethyl-1-[( 4-methoxycarbonylphenyl)methyl]-1H-imidazole $^1$H NMR (CDCl$_3$), δ: 0.85 (t, 3 H); 1.32 (m, 2 H); 1.65 (m, 2 H); 2.53 (t, 2 H); 3.91 (s, 3 H); 4.49 (s, 2 H); 5.27 (s, 2 H); 7.05 (d, 2 H); 8.01 (d, 2 H).

EXAMPLE 14

2-Butyl-4-chloro-5-chloromethyl-1-[( 2'-methoxycarbonyl-1,1'-biphenyl-4-yl)methyl]-1H-imidazole A solution of 1 g of 2-butyl-4-chloro-5-hydroxymethyl-1-[(2'-methoxycarbonyl-1,1'-biphenyl-4yl)methyl]-1H-imidazole in 20 ml of CHCl$_3$ is added with 1.44 g of thionyl chloride.

The mixture is stirred at room temperature for 2 hours then the solution is evaporated under reduced pressure and the residue is taken up and stripped more times with anhydrous toluene. The obtained crude product is triturated with ether to obtain 0.90 g of a ivory solid (80% yield).

M.p. 158°–159° C. $^1$H NMR (CDCl$_3$), δ: 0.93 (t, 3 H); 1.45 (m, 2 H); 1.80 (m, 2 H); 3.12 (t, 2 H); 3.70 (s, 3 H); 4.45 (s, 2 H); 5.43 (s, 2 H); 7.06–7.95 (m, 8 H).

The following compounds are prepared according to the same procedure:

2-butyl-4-chloro-5-chloromethyl-1H-imidazole $^1$H NMR (CDCl$_3$), δ: 0.90 (t, 3 H); 1.36 (m, 2 H); 1.89 (m, 2 H); 3.09 (t, 2 H); 4.68 (s, 2 H); 7.14 (s, 1 H).

EXAMPLE 15

2-butyl-4-chloro-1-[(2-methoxycarbonyl-1,1'-biphenyl-4-yl)methyl]-5-[(3-methoxycarbonylthien-2-yl)methoxymethyl]-1H-imidazole A suspension of 145 mg of 80% NaH in anhydrous THF heated to 60° C. is added with 1 g of 2-butyl-4-chloro-5-hydroxymethyl-1-[(2-methoxycarbonyl-1,1'-biphenyl-4-yl)methyl]-1H-imidazole dissolved in 8 ml of THF. The resulting solution is stirred at 60° C. for 1 h, cooled to 25° C. and 0.7 g of methyl 2-bromo-methylthien-3-yl-carboxylate are added dissolved in THF. After 1 hour the mixture is filtered and the solvent is evaporated off under reduced pressure. The crude product is purified by F.C. (eluent ethyl acetate/hexane 4:6). 0.84 g of a glassy oil are obtained (62% yield). $^1$H NMR (CDCl$_3$), δ: 0.88 (t, 3 H); 1.35 (m, 2 H); 1.67 (m, 2 H); 2.61 (t, 2 H); 3.64 (s, 3 H); 3.83 (s, 3 H); 4.53 (s, 2 H); 5.00 (s, 2 H); 5.24 (s, 2 H); 7.02–7.87 (m, 10 H).

The following compounds are prepared according to the same procedure:

2-butyl-4-chloro-5-[( 2-methoxycarbonylphenyl) methoxymethyl]-1-[[2'- ( 1-triphenylmethyl-tetrazol-5-yl) -1,1'-biphenyl-4-yl]methyl]-1H-imidazole $^1$H NMR (CDCl$_3$), δ: 0.84 (t, 3 H); 1.29 (m, 2 H); 1.63 (m, 2 H); 2.48 (t, 2 H); 3.85 (s, 3 H); 4.29 (s, 2 H); 4.79 (s, 2 H); 5.08 (s, 2 H); 6.72–7.98 (m, 27 H)

2-butyl-4-chloro-1-[(2-methoxycarbonyl-1,1'-biphenyl-4-yl)methyl]-5-[(3-methoxycarbonylfuran-2-yl) methoxymethyl]-1H-imidazole 2-butyl-4-chloro-5-[( 4-methoxycarbonylphenyl) methoxymethyl]-1-[( 2'-methoxycarbonyl-1,1'-biphenyl-4-yl)methyl]-1H-imidazole $^1$H NMR (CDCl$_3$), δ: 0.87 (t, 3 H); 1.32 (m, 2 H); 1.68 (m, 2 H); 2.57 (t, 2 H); 3.63 (s, 3 H); 3.89 (s, 3 H); 4.43 (s, 2 H); 4.49 (s, 2 H); 5.18 (s, 2 H); 6.95–7.99 (m, 12 H)

2-butyl-4-chloro-[(2'-methoxycarbonyl-1,1'-biphenyl-4-yl)methyl]-5-[( 2-methoxycarbonylphenyl)methoxymethyl]-1H-imidazole $^1$H NMR (CDCl$_3$), δ: 0.87 (t, 3 H); 1.34 (m, 2 H); 1.67 (m, 2 H); 2.57 (t, 2

H); 3.62 (s, 3 H); 3.86 (s, 3 H), 4.48 (s, 2 H); 4.86 (s, 2 H); 5.21 (s, 2 H); 6.98–7.95 (m, 12 H)

5-benzyloxymethyl-2-butyl-4-chloro-1-[[2'-( 1-triphenyl-methyltetrazol-5-yl)-1,1'-biphenyl-4-yl]methyl]-1H-imidazole $^1$H NMR (CDCl$_3$) δ: 0.85 (t, 3 H); 1 25 (m 2 H); 1 64 (m 2 H); 2.48 (t, 2 H); 4.22 (s, 2 H); 4.38 (s, 2 H); 5.02 (s, 2 H); 6.65–7.98 (m, 28 H)

2-butyl-4-chloro-1-[( 4-methoxycarbonylphenyl)methyl]-5-[( 2-methoxy-carbonylphenyl)methoxymethyl]-1H-imidazole $^1$H NMR (CDCl$_3$), δ: 0.84 (t, 3 H); 1.18 (m, 2 H); 1.50 (m, 2 H); 2.45 (t, 2 H); 3. 72 (s, 3 H); 3.91 (s, 3 H); 4.46 (s, 2 H); 4.80 (s, 2 H); 5.18 (s, 2 H); 6.80–8.00 (m, 8 H)

2-butyl-4-chloro-5-[(2-methoxycarbonylphenyl) methoxymethyl]-1-[[2-(2-methoxycarbonylphenyl)thien-5-yl]methyl]-1H-imidazole 2-butyl-4-chloro-5-[(2-methoxycarbonylphenyl) methoxymethyl]-1-[[4-(3-methoxycarbonylfuran-2-yl)phenyl]methyl]-1H-imidazole 2-butyl-4-chloro-5-[( 3-methoxycarbonylthien-2-yl) methoxymethyl]-1-[[2'-(1-triphenylmethyltetrazol-5-yl)-1,1'-biphenyl-4-yl]-1H-imidazole $^1$H NMR (CDCl$_3$) δ: 0.85 (t, 3 H); 1.34 (m, 2 H); 1.65 (m, 2 H); 2.49 (t, 2 H); 3.82 (s, 3 H); 4.33 (s, 2 H); 4.92 (s, 2 H); 5.08 (s, 2 H); 6.60–8.03 (m, 25 H).

2-butyl-4-chloro-5-[(3-methoxycarbonylfuran-2-yl) methoxymethyl]-1-[[2'-(1-triphenylmethyltetrazol-5-yl)-1,1'-biphenyl-4-yl]methyl]-1H-imidazole $^1$H NMR (CDCl$_3$), δ: 0.85 (t, 3 H); 1.28 (m, 2 H); 1.65 (m, 2 H); 2.47 (t, 2 H); 3.79 (s, 3 H); 4.28 (s, 2 H); 4.68 (s, 2 H); 5.03 (s, 2 H); 6.65–7.96 (m, 25 H)

2-butyl-4-chloro-5-(2-pyridyloxymethyl)-1-[[2'-(1-triphenylmethyltetrazol-5-yl) -1,1'-biphenyl-4-yl]methyl]-1H-imidazole 2-butyl-4-chloro-5-[(pyridin-2-yl)methoxymethyl]-1-[ [2'-(1-triphenylmethyltetrazol-5-yl)-1,1'-biphenyl-4-yl]methyl]-1H-imidazole.

EXAMPLE 16

2-butyl-4-chloro-1-[(2-methoxycarbonyl-1,1'-biphenyl-4-yl)methyl]-5-(2-methoxycarbonylphenoxymethyl)-1H-imidazole Method A A solution of 950 mg of 2-butyl-4-chloro-5-chloro-methyl-1-[(2-methoxycarbonylbiphenyl-4-yl)methyl]-1H-imidazole in 20 ml of anhydrous THF is added with 61 mf of 80% NaH, stirring for 2 hours at room temperature. The resulting solution is added with a solution of methyl salicylate sodium salt and a suspension of 122 mg of NaH in THF. The obtained mixture is heated to 60° C. and stirred at this temperature for 5 hours, then filtered and the solvent is evaporated off under reduced pressure. The crude is purified by F.C. (eluent ethyl acetate/hexane 4:6) and 550 mg of a thick oil are obtained (50% yield). $^1$H NMR (CDCl$_3$), δ: 0.89 (t, 3 H); 1.38 (m, 2 H); 1.72 (m, 2 H); 2.65 (t, 2 H); 3.63 (s, 3 H); 3.87 (s, 3 H), 4.94 (s, 2 H); 5.43 (s, 2 H); 6.95–7.90 (m, 12 H).

The following compounds are prepared according to the same procedure:

2-butyl-4-chloro-5-( 2-methoxycarbonylphenoxymethyl)-1H-imidazole $^1$H NMR (CDCl$_3$), δ: 0.91 (t, 3 H); 1.35 (m, 2 H); 1.65 (m, 2 H); 2.68 (t, 3 H); 4.95 (s, 2 H); 5.08 (s, 2 H); 6.6–7.7 (m, 5H)

2-butyl-4-chloro-1-[(2-methoxycarbonyl-1,1'-biphenyl-4-yl)methyl]-5-( 2-methoxycarbonylphenyltiomethyl)-1H-imidazole.

Method B solution of 323 mg of 2-butyl-4-chloro-5-( 2-methoxy carbonylphenoxymethyl)-1H-imidazole in 10 ml of anhydrous DMF is added with 30 mg of 80% NaH. The is stirred for 1 h at 25° C., then 310 mg of 4-(bromomethyl)-2'-(methoxycarbonyl)biphenyl dissolved in 5 ml of anhydrous DMF are added. The mixture is stirred for 24 h at 25° C., the solvent is evaporated off under reduced pressure. The product is separated from its regioisomer by F.C. (eluent:ethyl acetate/hexane 4:6) to obtain mg 200 of a thick oil (40% yield).

EXAMPLE 17

2-butyl-1-[(2-carboxy-1,1'-biphenyl-4-yl)methyl]-5-[(3-carboxythien-2-yl)methoxyethyl]-4-chloro-1H-imidazole A mixture of 0.83 g of 2-butyl-4-chloro-1-[( 2-methoxycarbonyl-1,1'-biphenyl-4-yl)methyl]-5-[(3-methoxycarbonylthien-2-yl)methoxymethyl]-1H-imidazole, 5.8 ml of 10% NaOH and 20 ml of ethanol is stirred at room temperature for 5 hours. The solvent is evaporated off under reduced pressure, the residue is taken up in 10 ml of H$_2$O and acidified to pH 4 with 5N HCl. A solid precipitates which is filtered and washed with H$_2$O. 0.6 of a white solid are obtained (77% yield ). M.p. 182°–185° C. $^1$H NMR (DMSO D$_6$), δ: 0.80 (t, 3 H); 1.25 (m, 2 H); 1.50 (m, 2 H); 2.54 (t, 2 H); 4.56 (s, 2 H); 4.97 (s, 2 H); 5.29 (s, 2 H); 7.11–7.76 (m, 10 H).

The following compounds are prepared according to the same procedure:

2-butyl-1-[(2-carboxy-1,1'-biphenyl-4-yl)methyl]-5-[(3-carboxyfuran-2-yl)methoxymethyl]-4-chloro-1H-imidazole 2-butyl-1-[(2-carboxy-1,1'-biphenyl-4-yl)methyl]-5-[(2-carboxyphenyl)methoxymethyl]-4-chloro-1H-imidazole, M.p. 177°–179° C. $^1$H NMR (DMSO D$_6$) δ: 0.80 (t, 3 H); 1.23 (m, 2 H); 1.54 (m, 2 H); 2.62 (t, 2 H); 5.09 (s, 2 H); 5.14 (s, 2 H); 6.60–7.75 (m, 12 H)

2-butyl-1-[(2-carboxy-1,1'-biphenyl-4-yl)methyl]-5-[(4-carboxyphenoxy)methoxymethyl]-4-chloro-1H-imidazole, M.p. 181°–183° C. $^1$H NMR (DMSO D$_6$) δ: 0.81 (t, 3 H); 1.24 (m, 2 H); 1.50 (m, 2 H); 2.53 (t, 2 H); 4.45 (s, 2 H); 4.51 (s, 2 H); 5.26 (s, 2 H); 6.95–7.92 (m, 12 H)

2-butyl-1-[(2-carboxy-1,1'-biphenyl-4-yl)methyl]-5-[(2-carboxyphenoxy)methyl]-4-chloro-1H-imidazole, M.p. >250° C. $^1$H NMR (DMSO D$_6$) δ: 0.81 (t, 3 H); 1.25 (m, 2 H); 1.51 (m, 2 H); 2.54 (t, 2 H); 4.48 (s, 2 H); 4.82 (s, 2 H); 5.28 (s, 2 H); 7.05–7.93 (m, 12 H)

2-butyl-5-[(2-carboxyphenyl)methoxymethyl]-1-[[2-( 2-carboxyphenyl)thien-5-yl]methyl]-4-chloro-1H-imidazole 2-butyl-5-[(2-carboxyphenyl)methoxymethyl]-1-[[4-(2-carboxyfuran-3-yl)phenyl]methyl]-4-chloro-1H-imidazole 2-butyl-1-[(4-carboxyphenyl)methyl]-1-[( 2-carboxyphenyl)methoxymethyl]-4-chloro-1H-imidazole. M.p. 163°–167° C. $^1$H NMR (DMSO D$_6$) δ: 0.85 (t, 3 H); 1.32 (m, 2 H); 1.58 (m, 2 H); 2.41 (t, 2 H); 4.45 (s, 2 H); 4.76 (s, 2 H); 5.26 (s, 2 H); 6.70–8.05 (m, 8 H)

2-butyl-1-[(2-carboxy-1,1'-biphenyl-4-yl)methyl]-5-(2-carboxyphenyltiomethyl)-4-chloro-1H-imidazole 2-butyl-5-[(3-carboxythien-2-yl)methoxymethyl]-4-chloro-1-[[2'-(1-triphenylmethyltetrazol-5-yl)-1,1'-biphenyl-4-yl]methyl]-1H-imidazole 2-butyl-5-[(3-carboxyfuran-2-yl)methoxymethyl]-4-chloro-1-[[2'-(1-triphenylmethyltetrazol-5-yl)-1,1'-biphenyl-4-yl]methyl]-1H-imidazole $^1$H NMR (CDCl$_3$), δ: 0.80 (t, 3 H); 1.23 (m, 2 H); 1.59 (m, 2 H ); 2.42 (t, 2 H); 4.27 (s, 2 H); 4.65 (s, 2 H); 4.98 (s, 2 H ); 6.65–7.85 (m, 25 H)

2-butyl-4-chloro-5-[(pyridin-2-yl)methoxymethyl]-1-[[2'-(1-triphenylmethyltetrazol-5-yl)-1,1'-biphenyl-4-yl]methyl]-1H-imidazole 2-butyl-4-chloro-5-(2-pyridyloxymethyl)-1-[[2'-(1-triphenylmethyltetrazol-5-yl)-1,1'-biphenyl-4-yl]methyl]-1H-imidazole 2-butyl-5-[(2-carboxyphenyl)methoxymethyl]-4-chloro-1-[[2'-(1-triphenylmethyltetrazol-5-yl)-1,1'-biphenyl-4-yl]methyl]-1H-imidazole $^1$H NMR (CDC;$_3$), δ: 0.85 (t, 3 H); 1.3 (m, 2 H); 1.65 (m, 2 H); 2.49 (t, 2 H); 4.22 (s, 2 H); 4.38 (s, 2 H); 5.02 (s, 2 H); 6.68–7.93 (m, 27 H).

EXAMPLE 18

2-butyl-5-[(2-carboxyphenyl)methoxymethyl]-4-chloro-1-[[2'-(1H-tetrazol-5-yl)-1,1'-biphenyl-4-yl]methyl]-1H-imidazole A mixture of 450 mg of 2-butyl-5-[( 2-carboxyphenyl)methoxymethyl]-4-chloro-1-[[2'-( 1-triphenylmethyltetrazol-5-yl)-1,1'-biphenyl-4-yl]methyl]-1H-imidazole, 7.5 ml of acetic acid, 3.7 ml of H$_2$O and 2 ml of THF is stirred at room temperature for 10 hours. The solvent s are evaporated off under reduced pressure and the residue is taken up in H$_2$O, alkalinized with 10% NaOH, an insoluble part is filtered off, the resulting solution is extracted with ether and acidified to pH 4.5 with 5N HCl. The obtained precipitate is filtered and washed with H$_2$O. 0.2 g of a white solid are obtained (70% yield). M.p. 109°–111° C. $^1$H NMR (CDCl$_3$), δ: 0.84 (t, 3 H); 1.27 (m, 2 H); 1.54 (m, 2 H); 2.39 (t, 2 H); 4.43 (s, 2 H); 4.60 (s, 2 H); 5.14 (s, 2 H); 6.80–8.12 (m, 12 H).

The following compounds are prepared according to the same procedure:

2-butyl-5-[(3-carboxythien-2-yl)methoxymethyl]-4-chloro-1-[[2'-(1H-tetrazol-5-yl)-1,1'-biphenyl-4-yl]methyl]-1H-imidazole M.p. 128°–133° C. (dec) $^1$H NMR (CDCl$_3$), δ: 0.84 (t, 3 H); 1.28 (m, 2 H); 1.54 (m, 2 H); 2.37 (t, 2 H); 4.48 (s, 2 H); 4.66 (s, 2 H); 5.12 (s, 2 H) ; 6.80–7.92 (m, 10 H).

2-butyl-5-[(3-carboxyfuran-2-yl)methoxymethyl-4-chloro-1-[[2'-(1H-tetrazol-5-yl)-1,1'-biphenyl-4-yl]methyl]-1H-imidazole, M.p. 137°–143° C. (dec.) $^1$H NMR (CDCl$_3$), δ: 0.789 (t, 3 H); 1.23 (m, 2 H); 1.52 (m, 2 H); 2.41 (t, 2 H); 4.35 (s, 2 H); 4.73 (s, 2 H); 4.97 (s, 2 H); 6.70–7.96 (m, 12 H)

2-butyl-4-chloro-5-[(pyridin-2-yl)methoxymethyl]-1-[[2'-(1H-tetrazol-5-yl)-1,1'-biphenyl-4-yl]methyl]-1H-imidazole 2-butyl-4-chloro-5-(2-pyridyloxymethyl)-1-[[2'-( 1H-tetrazol-5-yl)-1,1'-biphenyl-4-yl]methyl]-1H-imidazole 5-benzyloxymethyl-2-butyl-4-chloro-1-[[2'-(1H-tetrazol-5-yl)-1,1'-biphenyl-4-yl]methyl]-1H-imidazole, M.p. 98°–100° C. $^1$H NMR (CDCl$_3$), δ: 0.849 (t, 3 H); 1.26 (m, 2 H); 1.54 (m, 2 H); 2.34 (t, 2 H); 4.24 (s, 2 H); 4.38 (s, 2 H); 5.09 (s, 2 H); 6.70–8.05 (m, 13 H).

2-butyl-4-chloro-5-[(3-methoxycarbonylfuran-2-yl)methoxymethyl]-1-[[2'-(1H-tetrazol-5-yl)-1,1'-biphenyl-4-yl]methyl]-1H-imidazole M.p. 78°–82° C. $^1$H NMR (CDCl$_3$) δ: 0.83 (t, 3 H); 1.24 (m, 2 H); 1.55 (m, 2 H); 2.38 (t, 2 H); 3.70 (s, 3 H); 4.34 (s, 2 H); 4.67 (s, 2 H); 5.30 ( s, 2 H); 6.64 (d, 1 H); 6.81 (d, 2 H); 7.04 (d, 2 H); 7.30–7.61 (m, 4 H); 7.94 (m, 1 H).

2-butyl-4-chloro-5-[(3-methoxycarbonylthien-2-yl)methoxymethyl]-1-[[2'-(1H-tetrazol-5-yl)-1,1'-biphenyl-4-yl]methyl]-1H-imidazole M.D. 120°–125° C. $^1$H NMR (CDCl$_3$) δ: 0.85 (t, 3 H); 1.25 (m, 2 H); 1.57 (m, 2 H); 2.40 (t, 2 H); 3.77 (s, 3 H); 4.37 (s, 2 H); 4.87 (s, 2 H); 5.12 (s, 2 H); 6.83 (d, 2 H); 7.07 (d, 2 H); 7.14 (dd, 1 H); 7.37 (dd, 1 H); 7.56 (m, 2 H); 7.95 (m, 1 H).

2-butyl-4-chloro-5-[( 3-methoxycarbonylphenyl) methoxymethyl]-1-[[2'-(1H-tetrazol-5-yl)-1,1'-biphenyl-4-yl]methyl]-1H-imidazole M.p. 100°–110° C. (dec) $^1$H NMR (CDCl$_3$) δ: 0.85 (t, 3 H); 1,28 (m, 2 H); 1.58 (m, 2 H); 2.39 (t, 2 H); 3.81 (s, 3 H); 4.36 (s, 2 H); 4.76 (s, 2 H); 5.13 (s, 2 H); 6.86 (d, 2 H); 7.08 (d, 2 H); 7.28–8.03 (m, 8 H).

We claim:
1. A compound of formula (I)

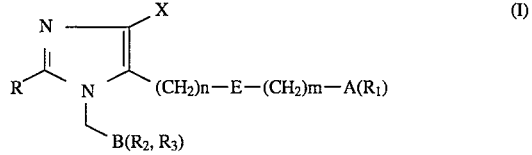

wherein

E is O or S;

R is C$_1$–C$_5$ straight, branched or cyclic alkyl or C$_2$–C$_5$ alkenyl;

X is H, F, Cl, Br, I, CF$_3$;

n is an integer 1 to 4;

m is an integer 0 to 4;

A and B are 5- or 6- membered aromatic carbocyclic rings optionally containing one or more heteroatoms selected from N, O, S and carrying the substituents R$_1$, R$_2$ and R$_3$, respectively; R$_1$ hydrogen, halogen, C$_1$–C$_5$ alkyl, alkoxy, hydroxyl, carboxyl, C$_1$–C$_4$ alkoxycarbonyl, a sulfonic group or a tetrazole group of formula

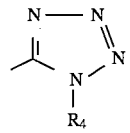

or

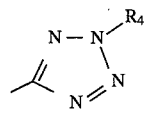

wherein R$_4$ is hydrogen or C$_1$–C$_5$ alkyl;

R$_2$ is hydrogen or a COOR$_4$ group (wherein R$_4$ is hydrogen or C$_1$–C$_5$ alkyl), CN, SO$_3$H, PO$_3$H or a tetrazole group;

R$_3$ is hydrogen or a moiety of formula II

wherein:

B', R'$_2$ have the same meanings above for B and R$_2$, R'$_3$ is H;

with the proviso that when A is phenyl, $R_1$ is different from H, and the pharmaceutically acceptable salts thereof.

2. A compound according to claim 1, wherein $A(R_1)$ is an aryl or heteroaryl ring selected from phenyl, thiophene, furan and pyridine, optionally substituted with a halogen atom, a $C_1-C_4$ alkyl group, a $C_1-C_4$ alkoxy, hydroxyl, carboxyl, $C_1-C_4$ alkoxycarbonyl or tetrazole group.

3. A compound according to claim 2, wherein $R_2$ is hydrogen or a $COOR_4$ group, wherein $R_4$ is as defined above; $R_3$ is hydrogen or an aryl or heteroaryl ring selected from phenyl, furan, thiophene, pyridine, thiazole optionally substituted with a carboxyl, $C_1-C_4$ alkoxycarbonyl, tetrazole group; n is 1 or 2; m is an integer 0 to 2.

4. A compound according to claim 1 selected from the group consisting of:

2-butyl-1-[2'-carboxy-1,1'-biphenyl-4-yl)methyl]-5-[(3-carboxythien-2-yl)methoxymethyl]-4-chloro-1H-imidazole;

2-butyl-5-[(2-carboxyphenyl)methoxymethyl]-4-chloro-1 [[2'-(1H-tetrazol-5-yl)-1,1'-biphenyl-4-yl]methyl]-1H-imidazole;

2-butyl-5-[(3-carboxythien-2-yl)methoxymethyl]-4-chloro-1-[(2'-(1H-tetrazol-5-yl)-1,1'-biphenyl-4-yl]methyl]-1H-imidazole;

2-butyl-5-[(3-carboxyfuran-2-yl)methoxymethyl-4-chloro-1-[[2'-(1H-tetrazol-5-yl)-1,1'-biphenyl-4-yl]methyl]-1H-imidazole;

2-butyl-4-chloro-5-[(pyridin-2-yl)methoxymethyl]-1-[[2'-(1H-tetrazol-5-yl)-1,1'-biphenyl-4-yl]methyl]-1H-imidazole;

2-butyl-4-chloro-5-(2-pyridinoxymethyl)-1-[[2'-( 1H-tetrazol-5-yl)1,1'-biphenyl-4-yl]methyl]-1H-imidazole;

2-butyl-1[(2'-carboxy-1,1'-biphenyl-4-yl)methyl]-5-[(3-carboxyfuran-2-yl)methoxymethyl]-4-chloro-1H-imidazole;

2-butyl-1-[(2'-carboxy-1,1'-biphenyl-4-yl]methyl]-5-[(2-carboxyphenyl) methoxymethyl]-4-chloro-1H-imidazole;

2-butyl-1-[(2'-carboxy-1,1'-biphenyl-4-yl) methyl]-5-[( 4-carboxyphenyl)methoxymethyl]-4-chloro-1H-imidazole;

2-butyl-1-[(2'-carboxy-1,1'-biphenyl-4-yl)methyl]-5-[( 2-carboxyphenoxy)methyl]-4-chloro-1H-imidazole;

2-butyl-5-[(2-carboxphenyl)methoxymethyl]-1-[[2-(2-carboxyphenyl) thien-5-yl]methyl]-4-chloro-1H-imidazole;

2-butyl-5-[(2-carboxyphenyl)methoxymethyl]-1-[[4-( 2-carboxyfuran-3-yl)phenyl]methyl]-4-chloro-1H-imidazole;

2-butyl-1-[(4-carboxyphenyl)methyl]-[1]5-[( 2-carboxyphenyl)methoxymethyl]-4-chloro-1H-imidazole;

2-butyl-4-chloro-5-[(2-methoxycarbonylphenyl) methoxymethyl]-1-[[2'-(1H-tetrazol-5-yl)-1,1'-biphenyl-4-yl]-methyl]-1H-imidazole;

2-butyl-4-chloro-5-[(3-methoxycarbonylfuran-2-yl) methoxymethyl]-1-[[2'-(1H-tetrazol-5-yl)-1,1'-biphenyl-4-yl]methyl]-1H-imidazole; and 2-butyl-4-chloro-5-[(3-methoxycarbonylthien-2-yl) methoxymethyl]-1-[[2'-( 1H-tetrazol-5-yl)-1,1'-biphenyl-4-yl]methyl]-1H-imidazole, and pharmaceutically acceptable salts thereof.

5. A pharmaceutic composition comprising as the active ingredient one compound of the claim 1 together with suitable pharmaceutical excipients.

6. A pharmaceutic composition comprising as the active ingredient one compound of claim 4 together with suitable pharmaceutical excipients.

* * * * *